(12) United States Patent
Liu et al.

(10) Patent No.: US 10,842,730 B2
(45) Date of Patent: Nov. 24, 2020

(54) HAIR CONDITIONING COMPOSITION AND A METHOD OF TREATING HAIR

(71) Applicant: Henkel AG & Co. KGaA, Duesseldorf (DE)

(72) Inventors: Conglin Liu, Shanghai (CN); Bruce Cox, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 154 days.

(21) Appl. No.: 15/565,418

(22) PCT Filed: Apr. 9, 2015

(86) PCT No.: PCT/CN2015/076140
§ 371 (c)(1),
(2) Date: Oct. 9, 2017

(87) PCT Pub. No.: WO2016/161588
PCT Pub. Date: Oct. 13, 2016

(65) Prior Publication Data
US 2018/0116948 A1 May 3, 2018

(51) Int. Cl.
*A61K 8/898* (2006.01)
*A61K 8/41* (2006.01)
*A61Q 5/12* (2006.01)
*A61K 8/73* (2006.01)

(52) U.S. Cl.
CPC .............. *A61K 8/898* (2013.01); *A61K 8/416* (2013.01); *A61K 8/731* (2013.01); *A61Q 5/12* (2013.01); *A61K 2800/5922* (2013.01)

(58) Field of Classification Search
None
See application file for complete search history.

(56) References Cited

FOREIGN PATENT DOCUMENTS

| WO | 2009016555 A2 | 2/2009 | |
|---|---|---|---|
| WO | 2015013779 A1 | 2/2015 | |
| WO | 2015013783 A1 | 2/2015 | |
| WO | WO-2015013779 A1 * | 2/2015 | ............. A61K 8/342 |
| WO | 2015027302 A1 | 3/2015 | |

OTHER PUBLICATIONS

State Intellectual Property Office of the P.R. China, International Search Report and Written Opinion issued in International Application No. PCT/CN2015/076140, dated Jan. 20, 2016.

* cited by examiner

*Primary Examiner* — Jake M Vu
(74) *Attorney, Agent, or Firm* — Lorenz & Kopf, LLP

(57) ABSTRACT

The present disclosure relates to a hair conditioning composition comprising a polyoxyalkylenated aminosilicone, a monoalkyl quaternary ammonium cationic surfactant and dialkyl acyloxyethyl hydroxyethylmonium cationic surfactant, and to a method of treating hair using the hair conditioning composition.

3 Claims, No Drawings

HAIR CONDITIONING COMPOSITION AND A METHOD OF TREATING HAIR

CROSS-REFERENCE TO RELATED APPLICATION

This application is a U.S. National-Stage entry under 35 U.S.C. § 371 based on International Application No. PCT/CN2015/076140, filed Apr. 9, 2015, which was published under PCT Article 21(2) and which is incorporated herein by reference in its entirety.

TECHNICAL FIELD

The present disclosure relates to a hair conditioning composition comprising a polyoxyalkylenated aminosilicone, a monoalkyl quaternary ammonium cationic surfactant and dialkyl acyloxyethyl hydroxyethylmonium cationic surfactant, and to a method of treating hair.

BACKGROUND

Polymers have been widely used in all kinds of cosmetics, e.g., both skin and hair treatment agents directly rinsed out or rinsed off again after their application (referred to as "rinse-off" products), as well as agents that are left on the skin or hair (referred to as "leave-on" agents). These polymers are intended to use for a variety of reasons and each specific property of the polymers is expected to achieve in the formulated product.

Usually, it is important for the thickening or conditioning properties of the polymers to be used in hair conditioning agents like shampoos. In addition, in these products, polymers also often serve as additives in order to improve or even make possible the deposition and fixing of other active substances and ingredients onto the skin or hair. In order to produce various effects of a hair conditioner, a plurality of polymers have to be added. However, this can lead to a series of drawbacks. Formulation problems can arise, for example, because the polymers react with one another or with other ingredients of the composition, resulting in precipitations or decompositions. Certain polymers also tend to continually precipitate out onto skin and particularly onto hair so that they are not completely removed by normal washing, causing an unwanted accumulation of the polymer and thereby a subsequent burden to the skin or hair.

EP 2170256 A2 discloses a conditioning composition comprising by weight: (a) from about 0.1% to about 10% of a surfactant system comprising: a dialkyl quaternized ammonium salt cationic surfactant; and a monoalkyl quaternized ammonium salt cationic surfactant; (b) from about 1% to about 15% of a high melting point fatty compound; (c) from about 0.1% to about 20% of an aminosilicone; (d) from about 0.1% to about 10% of a silicone resin; and (e) an aqueous carrier. However, the conditioning composition is still not entirely satisfactory as regards the properties of smoothness and softness to the hair conferred.

Accordingly, there is a need for an improved conditioning composition, which even containing a various types of polymers, simultaneously exhibits as many as possible of the desired properties of the composition and performance of hair treated by the composition.

BRIEF SUMMARY

One aspect of the present disclosure is a hair conditioning composition, comprising the components:

(a) from about 0.2% to about 4.0% by weight of a polyoxyalkylenated aminosilicone comprising repeating units of the formula:

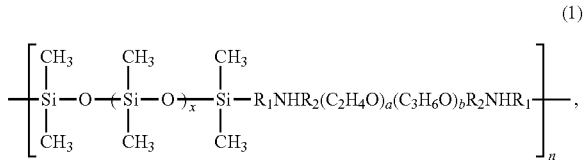

wherein,
a is an integer of from 1 to about 500,
b is an integer of from 0 to about 200,
$R_1$ is each independently a divalent organic group which is linked to the adjacent silicon atom via a carbon-silicon bond and to the nitrogen atom,
$R_2$ is each independently a divalent organic group which is linked to the adjacent oxygen atom via a carbon-oxygen bond and to the nitrogen atom, and
x is an integer chosen such that the siloxane block represents between about 50 and about 95 mol % based on the total weight of the polyoxyalkylenated aminosilicone,
n is an integer of from 1 to about 1,000;

(b) from about 0.5% to about 12.0% by weight of a monoalkyl quaternary ammonium cationic surfactant represented by the formula:

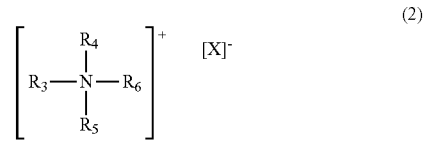

wherein $R_3$ is a linear or branched alkyl having 8 to 30 carbon atoms,
$R_4$ to $R_6$ each independently are an alkyl having 1 to 3 carbon atoms,
X is a salt forming anion selected from the group of halogen, acetate, citrate, lactate, glycolate, sulphate, and phosphate;

(c) from about 0.4% to about 5.0% by weight of a dialkyl acyloxyethyl hydroxyethylmonium cationic surfactant represented by the formula:

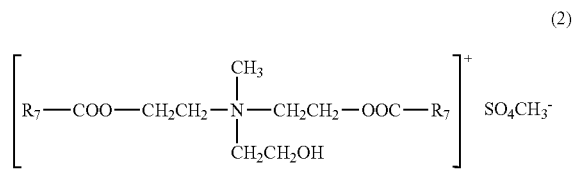

wherein $R_7$ is a linear or branched alkyl having 8 to 30 carbon atoms;

(d) from about 0.01% to about 2.0% by weight of a polymeric quaternary ammonium salt; and (e) from about 70% to about 98% by weight of an aqueous cosmetically acceptable carrier, wherein the weight percentages are based on the total weight of all components of the hair conditioning composition.

Another aspect of the present disclosure is method of treating hair comprising applying thereto a composition including the components as described above.

Other features and aspects of the subject matter are set forth in greater detail below.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It is to be understood by one of ordinary skill in the art that the present discussion is a description of exemplary embodiments only, and is not intended as limiting the broader aspects of the present disclosure.

Herein, "comprising" means that other steps and other components which do not affect the end result can be added. This term encompasses the terms "consisting of" and "consisting essentially of".

In one aspect, the present disclosure is generally directed to a hair conditioning composition, comprising the components:
(a) from about 0.2% to about 4.0% by weight of a polyoxyalkylenated aminosilicone comprising repeating units of the formula:

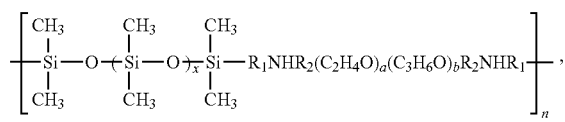

wherein,
a is an integer of from 1 to about 500,
b is an integer of from 0 to about 200,
$R_1$ is each independently a divalent organic group which is linked to the adjacent silicon atom via a carbon-silicon bond and to the nitrogen atom,
$R_2$ is each independently a divalent organic group which is linked to the adjacent oxygen atom via a carbon-oxygen bond and to the nitrogen atom, and
x is an integer chosen such that the siloxane block represents between about 50 and about 95 mol % based on the total weight of the polyoxyalkylenated aminosilicone,
n is an integer of from 1 to about 1,000;
(b) from about 0.5% to about 12.0% by weight of a monoalkyl quaternary ammonium cationic surfactant represented by the formula:

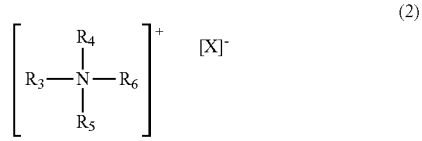

wherein $R_3$ is a linear or branched alkyl having 8 to 30 carbon atoms,
$R_4$ to $R_6$ each independently are an alkyl having 1 to 3 carbon atoms, X is a salt forming anion selected from the group of halogen, acetate, citrate, lactate, glycolate, sulphate, and phosphate;
(c) from about 0.4% to about 5.0% by weight of a dialkyl acyloxyethyl hydroxyethylmonium cationic surfactant represented by the formula:

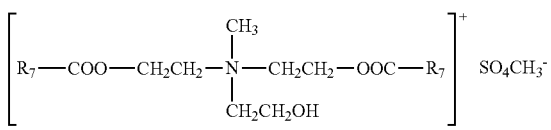

wherein $R_7$ is a linear or branched alkyl having 8 to 30 carbon atoms;
(d) from about 0.01% to about 2.0% by weight of a polymeric quaternary ammonium salt; and
(e) from about 70% to about 98% by weight of an aqueous cosmetically acceptable carrier,
wherein the weight percentages are based on the total weight of all components of the hair conditioning composition.

Component (a)

In accordance with the present disclosure, the hair conditioning composition comprises from about 0.2% to about 4.0% by weight of a polyoxyalkylenated aminosilicone comprising repeating units of the formula:

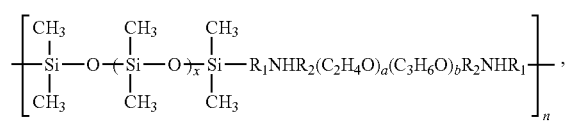

wherein,
a is an integer of from 1 to about 500, preferably from 5 to about 200, and more preferably from 5 to about 100;
b is an integer of from 0 to about 200, preferably from 4 to about 200, and more preferably from 5 to about 100;
$R_1$ is each independently a divalent organic group which is linked to the adjacent silicon atom via a carbon-silicon bond and to the nitrogen atom, preferably is a $C_2$ to $C_{12}$ hydrocarbonylene optionally containing one or more hetero atoms, selected from the group of ethylene, n-propylene, iso-propylene, n-butylene, iso-butylene, tert-butylene and —$CH_2CH_2CH_2OCH(OH)CH_2$—;
$R_2$ is each independently a divalent organic group which is linked to the adjacent oxygen atom via a carbon-oxygen bond and to the nitrogen atom, preferably is a $C_2$ to $C_{12}$ hydrocarbonylene optionally containing one or more hetero atoms, selected from the group of ethylene, n-propylene, iso-propylene, n-butylene, iso-butylene and tert-butylene, and
x is an integer chosen such that the siloxane block represents between about 50 and about 95 mol %, preferably about 70 and about 85 mol %, based on the total weight of the polyoxyalkylenated aminosilicone, more preferably is an integer of from 3 to about 500, in particular, 10 to about 300, and
n is an integer of from 1 to about 1,000, preferably 1 to about 500, and more preferably from 1 to about 200.

Moreover, it is particularly preferred if x is a number from 5 to about 300, a is a number from 5 to about 200, b a number from 4 to about 200, $R_1$ is a linear $C_{2-20}$ alkylene group and $R_2$ is a linear $C_{2-10}$ alkylene group, and, in each case, may be substituted by one or more OH groups and interrupted by one or more of non-adjacent O—, —C(O)—, —O—C(O)—, and —C(O)—O groups.

One particularly preferred is a copolymer of the general formula:

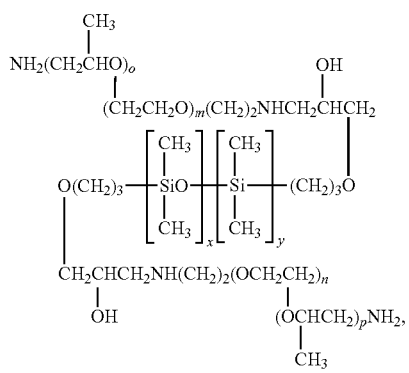

in which m and n, which may identical or different, represent an integer with the sum m+n having a mean value of 41 and o and p, which may be identical or different, represent an integer with the sum o+p having a mean value of 3.

The amine content in the polyoxyalkylenated aminosilicone is generally between about 0.02 and about 0.5 meq/g of copolymer in a solution at 30% in dipropylene glycol, and more particularly between about 0.05 and about 0.2.

The weight-average molecular weight of the silicone in the polyoxyalkylenated aminosilicone is preferably between about 5000 and about 1,000,000, and even more particularly between about 100,000 and about 200,000.

The polyoxyalkylenated aminosilicone can be prepared by processes known to those skilled in the art, for example by reaction of α,ω-diepoxy- or -dichloro-silicone with an α,ω-diamino polyoxyalkylene, or it is commercially available for example under the name of Silsoft® A-843 from Momentive Performance Materials Inc.

The polyoxyalkylenated aminosilicone is preferably used in an amount of about 0.3% to about 3.0% by weight based on the total weight of all components of the hair conditioning composition. More preferably, this amount is from about 0.5% to about 2.5% by weight. If the amount of polyoxyalkylenated aminosilicone is lower than about 0.2% by weight, the softness and smoothness of treated hair after drying may be deteriorated. If the amount is higher than 3.0% by weight, the composition cannot be completely removed by normal washing and the polymer may cause an overburden on the hair.

Component (b)

The hair conditioning composition according to the present disclosure also comprises about 0.5% to about 12.0% by weight of a monoalkyl quaternary ammonium cationic surfactant represented by the formula:

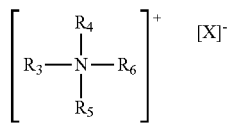

wherein $R_3$ is a linear or branched alkyl having 8 to 30 carbon atoms, preferably having 14 to 22 carbon atoms, for example octyl, nonyl, decyl, undecyl, 10-undecenyl, dodecyl, tridecyl, tetradecyl, pentadecyl, hexadecyl, hexadecenyl heptadecyl, heptadecenyl, octadecyl, 9-octadecenyl, 10,12-octadecadienyl, nonadecyl, 13-docosenyl, docosyl or triacontyl groups, in particular hexadecyl, hexadecenyl heptadecyl, heptadecenyl, octadecyl, 9-octadecenyl, 10,12-octadecadienyl.

$R_4$ to $R_6$ each independently are an alkyl having 1 to 3 carbon atoms, for example, methyl, ethyl, propyl, preferably all of $R_4$ to $R_6$ being methyl.

X is a salt forming anion selected from the group of halogen, acetate, citrate, lactate, glycolate, sulphate, and phosphate, preferably halogen, for example chloride.

Nonlimiting examples of such monoalkyl quaternary ammonium cationic surfactant include cetrimethyl ammonium chloride, steartrimonium chloride, behentrimonium chloride, stearamidopropyl trimonuim chloride, dioleoylethyl dimethyl ammonium methosulfate, and dioleoylethyl hydroxyethylmonium methosulfate, which can be used alone or in combination based on practical needs in the present disclosure.

The monoalkyl quaternary ammonium cationic surfactant are commonly used in cosmetic industry and are commercially available from for example Clariant under the trade name of Genamin STAC or Genamin KDMP, or from BASF under the trade name of Dehyquart A CA.

The monoalkyl quaternary ammonium cationic surfactant is preferably used in an amount of from about 0.8% to about 10.0% by weight based on the total weight of all components of the hair conditioning composition. More preferably, this amount is from about 1.0% to about 9.0% by weight. If the amount of monoalkyl quaternary ammonium cationic surfactant is lower than 0.5% by weight, the consistency of the product, the softness, combability and smoothness of hair in wet and dry conditions may not be satisfactory.

Component (c)

The hair conditioning composition as contemplated herein further comprises from about 0.4% to about 5.0% by weight of a dialkyl acyloxyethyl hydroxyethylmonium cationic surfactant represented by the formula:

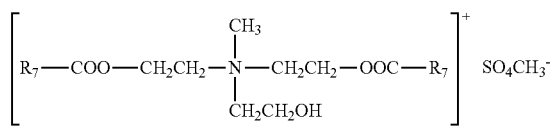

wherein $R_7$ is a linear or branched alkyl having 8 to 30 carbon atoms, preferably having 14 to 22 carbon atoms, for example octyl, nonyl, decyl, undecyl, 10-undecenyl, dodecyl, tridecyl, tetradecyl, pentadecyl, hexadecyl, hexadecenyl heptadecyl, heptadecenyl, octadecyl, 9-octadecenyl, 10,12-octadecadienyl, nonadecyl, 13-docosenyl, docosyl or triacontyl groups, in particular hexadecyl, hexadecenyl heptadecyl, heptadecenyl, octadecyl, 9-octadecenyl, 10,12-octadecadienyl.

The dialkyl acyloxyethyl hydroxyethylmonium cationic surfactant suitable as contemplated herein are commercially available from for example BASF under the trade name of Dehyquart F75, Dehyquart $C_{4086}$ and Dehyquart L80, and can be used singly or in combination according to practical needs.

The dialkyl acyloxyethyl hydroxyethylmonium cationic surfactant is preferably used in an amount of from about 0.5% to about 4.5% by weight based on the total weight of all components of the hair conditioning composition. More preferably, this amount is from about 0.6% to about 3.5% by weight. If the amount of dialkyl acyloxyethyl hydroxyethylmonium cationic surfactant is smaller than 0.4% by weight, the softness of treated hair may be deteriorated. If the amount is larger than 5.0% by weight, the consistency of the product may not be good enough to achieve the ease of use when shampooing or conditioning.

Component (d)

As contemplated herein, from about 0.01% to about 2.0% by weight of a polymeric quaternary ammonium salt is also contained in the hair conditioning composition.

The polymeric quaternary ammonium salts are those of well-known with their CTFA category name Polyquaternium. Typical examples of those are Polyquaternium 1, Polyquaternium 2, Polyquaternium 4, Polyquaternium 6, Polyquaternium 7, Polyquaternium 10, Polyquaternium 11, Polyquaternium 15, Polyquaternium 16, Polyquaternium 18, Polyquaternium 19, Polyquaternium 22, Polyquaternium 24, Polyquaternium 28, Polyquaternium 30, Polyquaternium 32, Polyquaternium 33, Polyquaternium 35, Polyquaternium 37, Polyquaternium 39, Polyquaternium 43, Polyquaternium 44, Polyquaternium 46, Polyquaternium 47, Polyquaternium 49, Polyquaternium 50, Polyquaternium 51, Polyquaternium 52, Polyquaternium 53, Polyquaternium 55, Polyquaternium 56, Polyquaternium 57, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium 70, Polyquaternium 71, Polyquaternium 72, Polyquaternium 73, Polyquaternium 74, Polyquaternium 75, Polyquaternium 76, Polyquaternium 77, Polyquaternium 78, Polyquaternium 79, Polyquaternium 80, Polyquaternium 81, Polyquaternium 82, Polyquaternium 83, Polyquaternium 84, Polyquaternium 85, Polyquaternium 86 and Polyquaternium 87, as well as well as silicone Polyquaternium 1, silicone Polyquaternium 2, silicone Polyquaternium 2 panthenol succinate, silicone Polyquaternium 3, silicone Polyquaternium 4, silicone Polyquaternium 5, silicone Polyquaternium 6, silicone Polyquaternium 7, silicone Polyquaternium 8, silicone Polyquaternium 9, silicone Polyquaternium 10, silicone Polyquaternium 11, silicone Polyquaternium 12, silicone Polyquaternium 15, silicone Polyquaternium 16, silicone Polyquaternium 16/Glycidoxy Dimethicone Crosspolymer, silicone Polyquaternium 17, silicone Polyquaternium 18, silicone Polyquaternium 20 and silicone Polyquaternium 21.

Preferably, Polyquaternium 10, Polyquaternium 37 and Polyquaternium 67, which are commercially available from Dow Chemicals can be used singly or in combination in the hair conditioning composition as contemplated herein.

As contemplated herein, the component (d) is preferably present in an amount of from about 0.05% to about 0.5%, preferably from about 0.1% to about 0.3% by weight based on the total weight of all components of the hair conditioning composition.

Component (e)

The hair conditioning composition also comprises a cosmetically acceptable carrier. The cosmetically acceptable carrier may be any carrier suitable for formulating other components into a composition being suitable for application onto hair. The carrier useful in the present disclosure includes water and water solutions of lower alkyl alcohols and polyhydric alcohols. The lower alkyl alcohols useful herein are monohydric alcohols having 1 to 6 carbons, more preferably ethanol and isopropanol. The polyhydric alcohols useful herein include propylene glycol, hexylene glycol, glycerin, and propane diol.

Preferably, the aqueous carrier is substantially water. Deionized or purified water is preferably used. Water from natural sources including mineral cations can also be used, depending on the desired characteristic of the product.

The hair conditioning composition may comprise from about 70% to v98% by weight of an aqueous cosmetically acceptable carrier, preferably from about 75% to about 95%, purified water by weight of the total weight of all components of the hair conditioning composition.

Other Components

The hair conditioning composition as contemplated herein may optionally comprises one or more other components, for example, protein hydrolyzates, preservatives, oily substances, non-ionic conditioning agents, fatty alcohols, moisturizers, chelating agents, and fragrance.

The composition as contemplated herein may also comprise protein hydrolyzates. Suitable protein hydrolyzates are preferably of plant, animal or marine origin.

Suitable animal protein hydrolyzates are e.g. elastin, collagen, keratin, silk and/or milk protein hydrolyzates, which can also be present in the form of salts. Products of this type are commercially available e.g. with the trade names Dehylan® from Cognis, Promois® from Interorgana, Collapuron® from Cognis, Nutrilan® from Cognis, Gelita-Sol® from Deutsche Gelatine Fabriken Stoess & Co, Lexein® from Inolexand Kerasol® from Croda.

Suitable protein hydrolyzates of plant origin are e.g. soybean, almond, rice, pea, potato, rapeseed and/or wheat protein hydrolyzates. Products of this type are available e.g. with the trade names Gluadin® from Cognis, DiaMin® from Diamalt, Lexein® from Inolex and Crotein® from Croda.

The suitable protein hydrolyzates of marine origin include e.g. collagen hydrolyzates from fish or algae and protein hydrolyzates from mussels or pearl hydrolyzates. Examples of suitable pearl hydrolyzates are the commercial products Pearl Protein Extract BG® or Crodarom® Pearl. Preferably, the protein hydrolyzates suitable for use in the present disclosure is hydrolyzed keratin available from Croda. If used in the composition, the protein hydrolyzates is present in an amount of from about 0.5% to about 0.01%, preferably from about 0.001% to about 0.005% by weight based on the total weight of all components of the hair conditioning composition.

The preservatives contained in the compositions as contemplated herein may include, but not be limited to, methylparaben, propylparaben, butylparaben, ethylparaben, potassium sorbate, trisodium EDTA, phenoxyethanol, ethyl alcohol, diazolidinyl urea, benzyl alcohol, and imidazolidinyl urea. Among them, methylparaben is preferred to be used in the composition.

If present in the composition as contemplated herein, the preservative is preferably present in an amount of from about 0.5% to about 0.01%, preferably from about 0.001% to about 0.005% by weight based on the total weight of all components of the hair conditioning composition.

Oily substances suitable for use in the composition are selected from such as silicone oils, either volatile or non-volatile, natural and synthetic oils. Among silicone oils those can be added to the compositions include dimethicone, e.g., Xiameter PMX-200 Fluid available from Dow Corning, dimethiconol, amodimethicone, e.g., XF-42 B1989 available from GE Toshiba Silicones, polydimethylsiloxane, cyclomethicone, e.g., Xiameter PMX-0245, natural oils such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate. Among them, silicone oils, for example, dimethicone are preferred to be used in the composition.

If present in the composition as contemplated herein, the oily substance is preferably present in an amount of from about 0.5% to about 10%, preferably from about 1% to about 5% by weight based on the total weight of all components of the hair conditioning composition.

Non-ionic conditioning agents suitable for the use in the present disclosure may be polyols such as glycerin, glycol and derivatives, polyethyleneglycoles known with trade names Carbowax PEG from Union Carbide and Polyox WSR range from Amerchol, polyglycerin, polyethyleneglycol mono- or di-fatty acid esters having general formula: $R_8CO(OCH_2CH_2)_nOH$ or $R_8CO(OCH_2CH_2)_nOOCR_9$, where $R_8$ and $R_9$ are independent from each other saturated, unsaturated or branched or non-branched alkyl chain with 7 to 21 carbon atoms and n is typically from 2 to about 100. Preferably, glycerin is used in the hair conditioning composition. If present in the composition as contemplated herein, the non-ionic conditioning agents is preferably present in an amount of from about 0.5% to about 10%, preferably from about 1% to about 5% by weight based on the total weight of all components of the hair conditioning composition.

The hair conditioning compositions comprise additionally at least one fatty alcohol having a saturated or unsaturated, branched or non-branched fatty acyl chain with from 8 to 24 carbon atoms. Concentration of fatty alcohols is usually less than about 20%, preferably less than about 15% by weight of all components of the composition. Typical examples to the most useful fatty alcohols are myristyl alcohol, palmityl alcohol, cetyl alcohol, stearyl alcohol, behenyl alcohol and their mixtures, for example cetearyl alcohol, which is preferred to be used in the composition.

The conditioning compositions of the present disclosure can also comprise moisturizers, chelating agents, and fragrance. The moisturizing agents are selected from panthenol, polyols, such as glycerol, polyethylene glycols with molecular weight of 200 to about 20,000. The moisturizing ingredients can be included in the hair conditioning compositions in an amount of from about 0.01% to about 2.5% by weight of all components of the composition.

The pH of the compositions as contemplated herein is suitably between about 3 and about 8 and preferably in the range of from about 3.5 to about 6.5.

The pH of the hair conditioning compositions can be adjusted with any organic and/or inorganic acids or their mixture. Non-limiting examples are phosphoric acid, hydrochloric acid as the inorganic ones and citric acid, lactic acid, glycolic acid, hydroxyacrylic acid, glyceric acid, malic acid, tartaric acid, malonic acid, succinic acid, glutaric acid, adipic acid, maleic acid, fumaric acid and phtalic acid as the organic acids.

The hair conditioning compositions as contemplated herein can take the form of leave-in or rinse out hair conditioners.

To use the rinse out compositions of the present disclosure to condition hair, one first wets the hair, then applies the composition as contemplated herein, then lathers the hair, and then rinses the hair. Alternatively, water and conditioner may be applied to the hair simultaneously. Conditioning with compositions may be done right after shampooing when the hair is still wet. Alternatively, conditioning the hair may be done separately from shampooing.

The compositions of the present disclosure may be leave-in conditioners. In such cases, the compositions are simply worked into the hair usually by using the fingers.

The compositions as contemplated herein may be prepared by methods which are known to those skilled in the art.

The hair conditioning compositions of the present disclosure can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbon dioxide, dimethylether and alkanes such as butane propane or their mixtures.

The hair conditioning compositions of the present invention can be in the for of emulsions, solutions, gels and dispersions. In the case that solutions and/or gels forms are preferred the appearance can be either with a transparent or opaque. As a product form, foam is as well suited when packed into a pressurized can or delivered through a pump-foamer (non-aerosol). In the case that an aerosol foam preparation is preferred, propellant gas must be added to the formulation. The suitable propellant gasses are carbon dioxide, dimethylether and alkanes such as butane, propane, isobutane or their mixtures.

The following examples are intended to assist one skilled in the art to better understand and practice the present disclosure. The scope of the present disclosure is not limited by the examples but is defined in the appended claims. All parts and percentages are based on weight unless otherwise stated.

EXAMPLES

Materials

Polyquaternium-10 is commercially available from Dow Chemical;

Polyquaternium-67 is commercially available from Dow Chemical;

Methylparaben is commercially available from Clariant;

Behentrimonium chloride is commercially available from Evonik;

Steartrimonium chloride is commercially available from Clariant;

Cetrimonium chloride is commercially available from BASF;

Glycerin is commercially available from Emery;

Lactic acid is commercially available from Purac Biochem;

Citric acid is commercially available from Anhui Ante;

Cetearyl alcohol is commercially available from BASF;

Cetyl alcohol is commercially available from BASF;

Behenyl alcohol is commercially available from BASF;

Dehyquart F 75 is commercially available from BASF (68% by weight active);

Dehyquart C4086 is commercially available from BASF (30% by weight active);

Dehyquart L 80 is commercially available from BASF (76.5% by weight active);

Isopropyl myristate is commercially available from BASF;

Dicaprylyl carbonate is commercially available from BASF;

Dimethicone is commercially available from Dow Corning;

XF-42-B1989 is commercially available from Momentive;

KF-9008 is commercially available from Shin-Etsu;

Silsoft A-843 is commercially available from Momentive (30% by weight active);

Xiameter PMX-1503 Fluid is commercially available from Dow Corning;

Parfum is commercially available from Symrise;

Panthenol is commercially available from Zhejiang Xinfu;

Phenoxyethanol is commercially available from Dow Chemical;

Hydrolyzed keratin is commercially available from Croda;

Aqua is purified water.

The compositions of Examples 1 to 16 (E1 to E16) and Comparative Examples 1 to 5 (CE1 to CE5) are shown in Tables 1 and 2, respectively.

The inventive examples and comparative examples are prepared as follows: Polyquaternium-10 or Polyquaternium-67 was added to purified water and mixed to hydrate the polymer. The rest of materials in Group 1 were added into the polymer. The mixture then was added to 80° C. until it was dissolved and homogeneous (water phase). The materials in Group 2 were heated to 75° C. in a separate vessel until they were melted and homogeneous (oil phase). The oil phase was then added to the water phase by using a homogenizer. The resulting mixture was then cooled to 55° C. by using a propeller stirrer. The materials in Group 3 were added one by one with intensive agitating. Then, the batch was cooled to below 40° C. with stirring and the materials in Group 4 were then added and the product was obtained to weight by using purified water.

TABLE 1

Compositions of Inventive Examples (E1 to E16)

| Group | Component | E1 | E2 | E3 | E4 | E5 | E6 | E7 | E8 |
|---|---|---|---|---|---|---|---|---|---|
| Group 1 | Aqua | to 100 | to 100 | to 100 | to 100 | to 100 | to 100 | to 100 | to 100 |
|  | Polyquaternium-10 | 0.1 | — | — | 0.1 | — | 0.1 | — | — |
|  | Polyquaternium-67 | — | 0.1 | 0.1 | — | 0.15 | — | 0.1 | 0.15 |
|  | Methylparaben | 0.3 | 0.3 | 0.3 | 0.3 | 0.3 | 0.3 | 0.3 | 0.3 |
|  | Behentrimonium Chloride | 2.5 | — | — | 2.5 | 3.5 | 4.0 | 5.0 | 3.5 |
|  | Steartrimonium Chloride | — | 3.0 | 3.0 | — | — | — | 2.5 | — |
|  | Glycerin | 0.5 | 0.8 | 0.8 | 0.5 | 1.5 | 0.8 | 0.8 | 1.5 |
|  | Dehyquart L 80 | — | — | — | 1.0 | — | — | — | 1.0 |
|  | Lactic Acid | 0.6 | — | — | — | — | — | — | — |
|  | Citric Acid | — | 0.2 | 0.2 | 0.1 | 0.05 | 0.1 | 0.1 | 0.05 |
| Group 2 | Cetearyl Alcohol | 4.5 | 5.0 | 4.5 | 4.5 | — | — | — | — |
|  | Cetyl alcohol | — | — | — | — | 4.0 | 4.0 | 4.0 | 4.5 |
|  | Behenyl alcohol | — | — | — | — | 4.0 | 4.0 | 4.0 | 4.5 |
|  | Dehyquart F 75 | 1.5 | 1.5 | — | 1.0 | — | 2.0 | 2.0 | 2.0 |
|  | Dehyquart C4086 | — | — | 4.0 | — | 3.5 | — | — | — |
|  | Isopropyl Myristate | 1.5 | 2.0 | 2.0 | 1.5 | — | — | — | — |
|  | Dicaprylyl Carbonate | — | — | — | — | 2.5 | 2.5 | 2.5 | 2.5 |
| Group 3 | Dimethicone | 0.5 | 1.5 | 1.5 | 0.5 | 1.0 | 0.5 | — | — |
|  | KF-9008 | — | — | — | — | — | — | 2.0 | — |
|  | Xiameter PMX-1503 Fluid | — | — | — | — | — | 4.0 | — | 4.0 |
|  | Silsoft A-843 | 2.0 | 2.5 | 2.5 | 2.0 | 2.5 | 2.0 | 2.5 | 2.0 |
|  | XF-42-B1989 | 1.0 | — | 0.8 | 1.0 | 1.5 | — | 1.5 | — |
| Group 4 | Parfum | 0.3 | 0.35 | 0.35 | 0.3 | 0.5 | 0.5 | 0.5 | 0.5 |
|  | Cetrimonium Chloride | — | 0.5 | 0.5 | 0.5 | 0.8 | 0.8 | 0.8 | 0.8 |
|  | Panthenol | 0.15 | 0.15 | 0.15 | 0.15 | 0.15 | 0.15 | 0.15 | 0.15 |
|  | Phenoxyethanol | 0.4 | 0.4 | 0.4 | 0.4 | 0.4 | 0.4 | 0.4 | 0.4 |
|  | Hydrolyzed Keratin | 0.001 | 0.001 | 0.001 | 0.001 | 0.002 | 0.002 | 0.002 | 0.002 |

| Group | Component | E9 | E10 | E11 | E12 | E13 | E14 | E15 | E16 |
|---|---|---|---|---|---|---|---|---|---|
| Group 1 | Aqua | to 100 | to 100 | to 100 | to 100 | to 100 | to 100 | to 100 | to 100 |
|  | Polyquaternium-10 | 0.1 | 0.1 | 0.1 | 0.1 | 0.1 | 0.1 | 0.1 | 0.1 |
|  | Polyquaternium-67 | — | — | — | — | — | — | — | — |
|  | Methylparaben | 0.3 | 0.3 | 0.3 | 0.3 | 0.3 | 0.3 | 0.3 | 0.3 |
|  | Behentrimonium Chloride | — | 1.0 | 5.0 | 8.0 | 1.0 | 1.0 | 1.0 | 1.0 |
|  | Steartrimonium Chloride | 2.5 | — | — | — | — | — | — | — |
|  | Glycerin | 0.5 | 0.5 | 0.5 | 0.5 | 0.5 | 0.5 | 0.5 | 0.5 |
|  | Dehyquart L 80 | — | — | — | — | — | — | — | — |
|  | Lactic Acid | — | 0.6 | 0.6 | 0.6 | 0.6 | 0.6 | 0.6 | 0.6 |
|  | Citric Acid | 0.02 | — | — | — | — | — | — | — |

TABLE 1-continued

Compositions of Inventive Examples (E1 to E16)

| Group | Component | | | | | | | | |
|---|---|---|---|---|---|---|---|---|---|
| Group 2 | Cetearyl Alcohol | 4.0 | 4.5 | 4.5 | 4.5 | 4.5 | 4.5 | 4.5 | 4.5 |
| | Cetyl alcohol | — | — | — | — | — | — | — | — |
| | Behenyl alcohol | — | — | — | — | — | — | — | — |
| | Dehyquart F 75 | — | 1.5 | 1.5 | 1.5 | 1.0 | 5.0 | 1.5 | 1.5 |
| | Dehyquart C4086 | 2.0 | — | — | — | — | — | — | — |
| | Isopropyl Myristate | 0.8 | 1.5 | 1.5 | 1.5 | 1.5 | 1.5 | 1.5 | 1.5 |
| | Dicaprylyl Carbonate | — | — | — | — | — | — | — | — |
| Group 3 | Dimethicone | 0.5 | 0.5 | 0.5 | 0.5 | 0.5 | 0.5 | 0.5 | 0.5 |
| | KF-9008 | — | — | — | — | — | — | — | — |
| | Xiameter PMX-1503 Fluid | — | — | — | — | — | — | — | — |
| | Silsoft A-843 | 0.5 | 2.0 | 2.0 | 2.0 | 2.0 | 2.0 | 5.0 | 8.0 |
| | XF-42-B1989 | — | 1.0 | 1.0 | 1.0 | 1.0 | 1.0 | 1.0 | 1.0 |
| Group 4 | Parfum | 0.3 | 0.3 | 0.3 | 0.3 | 0.3 | 0.3 | 0.3 | 0.3 |
| | Cetrimonium Chloride | — | — | — | — | — | — | — | — |
| | Panthenol | 0.15 | 0.15 | 0.15 | 0.15 | 0.15 | 0.15 | 0.15 | 0.15 |
| | Phenoxyethanol | 0.4 | 0.4 | 0.4 | 0.4 | 0.4 | 0.4 | 0.4 | 0.4 |
| | Hydrolyzed Keratin | 0.001 | 0.001 | 0.001 | 0.001 | 0.001 | 0.001 | 0.001 | 0.001 |

TABLE 2

Compositions of Comparative Examples (CE1 to CE5)

| Group | Component | CE1 | CE2 | CE3 | CE4 | CE5 |
|---|---|---|---|---|---|---|
| Group 1 | Aqua | to 100 | to 100 | to 100 | to 100 | to 100 |
| | Polyquaternium-10 | 0.1 | 0.1 | 0.1 | 0.1 | 0.1 |
| | Methylparaben | 0.3 | 0.3 | 0.3 | 0.3 | 0.3 |
| | Behentrimonium Chloride | 0.1 | 2.5 | 2.5 | 2.5 | 2.5 |
| | Glycerin | 0.5 | 0.5 | 0.5 | 0.5 | 0.5 |
| | Lactic Acid | 0.6 | 0.6 | 0.6 | 0.6 | 0.6 |
| Group 2 | Cetearyl Alcohol | 4.5 | 4.5 | 4.5 | 4.5 | 4.5 |
| | Dehyquart F 75 | 1.5 | 0.5 | 8.0 | 1.5 | 1.5 |
| | Isopropyl Myristate | 1.5 | 1.5 | 1.5 | 1.5 | 1.5 |
| Group 3 | Dimethicone | 0.5 | 0.5 | 0.5 | 0.5 | 0.5 |
| | Silsoft A-843 | 2.0 | 2.0 | 2.0 | 0.1 | 0.5 |
| | XF-42-B1989 | 1.0 | 1.0 | 1.0 | 1.0 | 1.0 |
| Group 4 | Parfum | 0.3 | 0.3 | 0.3 | 0.3 | 0.3 |
| | Panthenol | 0.15 | 0.15 | 0.15 | 0.15 | 0.15 |
| | Phenoxyethanol | 0.4 | 0.4 | 0.4 | 0.4 | 0.4 |
| | Hydrolyzed Keratin | 0.001 | 0.001 | 0.001 | 0.001 | 0.001 |

Evaluation:

The testing method was performed by the following steps:
1: Choose subjects having Asian hairs with normal or high level of damage to be subjected to the tests;
2: Wet the hair with warm water, and then apply 6 to 8 g shampoo (depending on the hair length of the subject) on the wet hair to lather and foam, and then rinse the hair copiously with warm water;
3: Apply 12 to 14 g hair conditioning composition to be tested (depending on the hair length of the subject) on the shampooed hair from the middle of hair to the ends of hair, spread the hair conditioning composition on the hair evenly, and rinse the conditioned hair copiously with warm water;
4: Dry the wet hair with a towel; and
5: Dry the hair completely with a hairdryer.

A panel of 4 professional hairdressers evaluated the properties of the hair conditioning compositions, including for example consistency, distribution on hair when applying, and the performance of hair, including smoothness, softness, combability in wet and dry conditions and appearance such as shine, heaviness, etc. The performances of each are sorted by level 0 to 6 as below, which was averaged by the total scores of the panel. The higher the number is, the better the performance is. If any performance of a composition is lower than 4, the composition is considered as not fulfilling the satisfaction of a person skilled in the art.

6: Very good,

5: Good,

4: Slightly good,

3: Slightly bad,

2: Bad, and

1: Very bad.

The results of the evaluation were listed in Table 3.

As can been seen in Table 3, compared to CE1 having lower amount of monoalkyl quaternary ammonium cationic surfactant, E1, E10 to E12 exhibited much better results in softness of hair, and the consistency and distribution on hair of CE1 were not acceptable. Compared to CE2 having a lower amount of dialkyl acyloxyethyl hydroxyethylmonium cationic surfactant, E1, E13 and E14 exhibited a better result in softness of towel dried hair. Although CE3 which contains an excessively high amount of dialkyl acyloxyethyl hydroxyethylmonium cationic surfactant also exhibited an acceptable hair feel after conditioning, the consistency is not satisfactory and was not easy to use when conditioning. Compared to CE4 and CE5 having a lower amount of polyoxyalkylenated aminosilicone, E1, E15 and E16 exhibited a much better result of dry hair feel in softness, smoothness and heaviness.

TABLE 3

Panel test results of the examples

| Test item | E1 | E10 | E11 | E12 | E13 | E14 | E15 | E16 | CE1 | CE2 | CE3 | CE4 | CE5 |
|---|---|---|---|---|---|---|---|---|---|---|---|---|---|
| Consistency | 5 | 4 | 5 | 5 | 5 | 5 | 5 | 5 | 3 | 4 | 3 | 5 | 5 |
| Smoothness of hair when applying | 5 | 4 | 5 | 5 | 5 | 5 | 6 | 6 | 3 | 4 | 4 | 3 | 4 |
| Distribution on hair when applying | 5 | 4.5 | 5 | 5 | 5 | 5 | 6 | 6 | 3 | 4 | 4 | 3 | 4 |
| softness of towel dried hair | 5 | 4 | 5 | 5 | 4 | 5 | 5 | 5 | 3 | 3 | 5 | 3 | 4 |
| Finger through when drying | 5 | 5 | 5 | 5 | 5 | 5 | 6 | 6 | 4 | 4 | 5 | 3 | 4 |
| Combability when blow drying | 5 | 5 | 5 | 5 | 5 | 5 | 6 | 6 | 4 | 5 | 5 | 3 | 4 |
| Look of dry hair, not flying away | 5 | 4.5 | 5 | 5 | 5 | 5 | 5 | 5 | 4 | 4 | 5 | 3 | 4 |
| Shine | 5 | 5 | 5 | 5 | 5 | 5 | 5 | 5 | 4 | 5 | 5 | 3 | 4 |
| Softness of dry hair | 5 | 4 | 5 | 5 | 5 | 5 | 5 | 5 | 3 | 4 | 5 | 3 | 3 |
| Smoothness of dry hair | 5 | 4.5 | 5 | 5 | 5 | 5 | 6 | 6 | 4 | 5 | 5 | 3 | 3 |
| Combability after drying | 5 | 5 | 5 | 5 | 5 | 5 | 5 | 5 | 4 | 4 | 5 | 3 | 4 |
| Moisture of dry hair ends | 5 | 5 | 5 | 5 | 5 | 5 | 5 | 5 | 4 | 5 | 5 | 3 | 3 |
| Heaviness of dry hair | 5 | 5 | 5 | 5 | 5 | 5 | 5 | 5 | 4 | 4 | 5 | 3 | 3 |
| Non overburdening | 5 | 5 | 5 | 5 | 5 | 5 | 5 | 4 | 5 | 5 | 5 | 5 | 5 |
| Static electricity control | 5 | 5 | 5 | 5 | 5 | 5 | 5 | 5 | 4 | 5 | 5 | 5 | 5 |

These and other modifications and variations of the present disclosure may be practiced by those of ordinary skill in the art, without departing from the spirit and scope of the present disclosure. In addition, it should be understood that aspects of the various embodiments may be interchanged both in whole or in component. Furthermore, those of ordinary skill in the art will appreciate that the foregoing description is by way of example only, and is not intended to limit the present disclosure so further described in such appended claims.

What is claimed is:

1. A hair conditioning composition, consisting of the components:
   (a) from about 0.5% to about 2.5% by weight of Silsoft A-843
   (b) from about 1.0% to about 8.0% by weight of a monoalkyl quaternary ammonium cationic surfactant selected from the group of cetrimonium chloride, behentrimonium chloride, steartrimonium chloride, and combinations thereof
   (c) from about 1.0% to about 5.0% by weight of a dialkyl acyloxyethyl hydroxyethylmonium cationic surfactant selected from the group of Dehyquart F 75, Dehyquart C4086, Dehyquart L 80, and combinations thereof;
   (d) from about 0.01% to about 0.15% by weight of a polymeric quaternary ammonium salt selected from the group of Polyquaternium-10, Polyquaternium-67, and combinations thereof;
   (e) from about 70% to about 98% by weight of water; and optionally
   (f) one or more ingredients selected from the group of methylparaben, glycerin, lactid acid, citric acid, cetearyl alcohol, cetyl alcohol, behenyl alcohol, isopropyl myristate, dicaprylyl carbonate, dimethicone, KF-9008, Xiameter PMX-1503 Fluid, XF-48-B1989, perfume, panthenol, phenoxyethanol, and hydrolyzed keratin,
   wherein the weight percentages are based on the total weight of all components of the hair conditioning composition.

2. The hair conditioning composition according to claim 1, wherein the component (a) is present in an amount of about 2.0% by weight based on the total weight of all components of the hair conditioning composition.

3. A method of treating hair comprising:
   applying to the hair a composition consisting of the like components:
   (a) from about 0.5% to about 2.5% by weight of Silfoft A-843
   (b) from about 1.0% to about 8.0% by weight of a monoalkyl quaternary ammonium cationic surfactant selected from the group of cetrimonium chloride, behentrimonium chloride, steartrimonium chloride, and combinations thereof;
   (c) from about 1.0% to about 5.0% by weight of a dialkyl acyloxyethyl hydroxyethylmonium cationic surfactant selected from the group of Dehyquart F 75, Dehyquart C4086, Dehyquart L 80, and combinations thereof;
   (d) from about 0.01% to about 0.15% by weight of a polymeric quaternary ammonium salt selected from the group of Polyquaternium-10, Polyquaternium-67, and combinations thereof;
   (e) from about 70% to about 98% by weight of water and optionally
   (f) one or more ingredients selected from the group of methylparaben, glycerin, lactid acid, citric acid, cetearyl alcohol, cetyl alcohol, behenyl alcohol, isopropyl myristate, dicaprylyl carbonate, dimethicone, KF-9008, Xiameter PMX-1503 Fluid, XF-42-B1989, perfume, panthenol, phenoxyethanol, and hydrolyzed keratin,
   wherein the weight percentages are based on the total weight of all components of the hair conditioning composition.

* * * * *